United States Patent
Knepper et al.

(10) Patent No.: US 10,286,168 B2
(45) Date of Patent: May 14, 2019

(54) PHENOTYPING OF SLEEP BREATHING DISORDERS USING A BREATHING THERAPY MACHINE

(71) Applicant: DeVilbiss Healthcare LLC, Somerset, PA (US)

(72) Inventors: Michael B. Knepper, Friedens, PA (US); James P. Froehlich, Berlin, PA (US); Robert Joseph Thomas, Newton, MA (US); Joseph J. Boring, Davidsville, PA (US)

(73) Assignee: DEVILBISS HEALTHCARE LLC, Somerset, PA (US)

( * ) Notice: Subject to any disclaimer, the term of this patent is extended or adjusted under 35 U.S.C. 154(b) by 773 days.

(21) Appl. No.: 14/334,132

(22) Filed: Jul. 17, 2014

(65) Prior Publication Data

US 2016/0015917 A1   Jan. 21, 2016

(51) Int. Cl.
*A61M 16/00* (2006.01)

(52) U.S. Cl.
CPC ...... *A61M 16/0069* (2014.02); *A61M 16/024* (2017.08); *A61M 2016/0039* (2013.01); *A61M 2205/3365* (2013.01); *A61M 2205/52* (2013.01); *A61M 2205/60* (2013.01)

(58) Field of Classification Search
CPC .............. A61M 16/00; A61M 16/0051; A61M 16/0069; A61M 2205/60; A61M 2205/52; A61M 2205/3375; A61B 5/68; A61B 5/113
USPC .................................................... 128/204.23
See application file for complete search history.

(56) References Cited

U.S. PATENT DOCUMENTS

| | | |
|---|---|---|
| 5,645,054 A | 7/1997 | Cotner et al. |
| 7,468,040 B2 | 12/2008 | Hartley et al. |
| 7,469,697 B2 | 12/2008 | Lee et al. |
| 7,662,101 B2 | 2/2010 | Lee et al. |
| 7,787,946 B2 | 8/2010 | Stahmann et al. |
| 7,942,824 B1* | 5/2011 | Kayyali .......... A61B 5/021 600/538 |
| 8,221,327 B2 | 7/2012 | Lee et al. |
| 8,276,585 B2 | 10/2012 | Buckley et al. |
| 2003/0111079 A1* | 6/2003 | Matthews ........ A61M 16/0051 128/204.18 |
| 2005/0217674 A1 | 10/2005 | Burton et al. |
| 2006/0266356 A1* | 11/2006 | Sotos ............... A61B 5/4557 128/204.23 |
| 2007/0129647 A1 | 6/2007 | Lynn |
| 2009/0082639 A1 | 3/2009 | Pittman et al. |
| 2010/0313898 A1 | 12/2010 | Richard et al. |

(Continued)

FOREIGN PATENT DOCUMENTS

| | | |
|---|---|---|
| EP | 2008581 A2 | 12/2008 |
| WO | 2009/042454 A1 | 4/2009 |

OTHER PUBLICATIONS

Extended European Search Report dated Feb. 26, 2018, corresponding to counterpart European Application No. 15821762.0; 11 pages.

*Primary Examiner* — Gregory A Anderson
*Assistant Examiner* — Margaret M Luarca
(74) *Attorney, Agent, or Firm* — Carter, Deluca, Farrell & Schmidt, LLP

(57) ABSTRACT

An improvement for existing breathing therapy machines which allows the machine to determine a patient's dominant respiratory phenotype using an auto-titration mode and flow sensor.

12 Claims, 4 Drawing Sheets

(56) References Cited

U.S. PATENT DOCUMENTS

| | | |
|---|---|---|
| 2011/0061647 A1 | 3/2011 | Stahmann et al. |
| 2011/0192400 A9 | 8/2011 | Burton et al. |
| 2012/0010519 A1 | 1/2012 | Rapoport et al. |
| 2012/0247472 A1 | 10/2012 | Lynch, Jr. |

* cited by examiner

|  | Average Pressure | Number of Events | Number of Central Events | Condition | Pressure Change | Phenotype Decision |
|---|---|---|---|---|---|---|
| 1 | Down | Down | Down/None | C<O | (0.20) | Stable |
| 2 | None | Down | Down/None | C<O | (0.20) | Stable |
| 3 | Down | None | Down | C<O | (0.50) | Stable |
| 4 | Up | Down | Down/None | C<O | 0.10 | Linear Obstructive |
| 5 | Down | None | None | C<O | (0.50) | Linear Obstructive |
| 6 | None | None | Down/None | C<O | (0.10) | Stable |
| 7 | Up | None | Down/None | C<O | 0.10 | Non-Responsive Obstructive |
| 8 | Up | Up | Down/None | C<O | 0.60 | REM / Positional |
| 9 | None | Up | Down/None | C<O | 0.20 | REM / Positional |
| 10 | Down | Up | Down/None | C<O | 0.50/0.20 | REM / Positional |
| 11 | X | X | Up | C<O | (0.50) | Central |
| 12 | X | X | X | C>O | (0.20) | Central |

FIG. 4

PHENOTYPING OF SLEEP BREATHING DISORDERS USING A BREATHING THERAPY MACHINE

FIELD OF THE INVENTION

This invention is related to the field of breathing therapy machines, such as continuous positive airway pressure (CPAP) or bi-level (adaptive or non-adaptive) positive airway pressure (Bi-PAP) machines of the type typically used to treat patients suffering from breathing disorders, such as hypopnea or apnea, and, in particular, is related to the use of such a machine for the phenotyping of a patient's sleep-breathing disorder.

BACKGROUND OF THE INVENTION

Continuous Positive Airways Pressure (CPAP) machines are well known in the art for use in the treatment of a number of respiratory conditions, such as sleep apnea and hypopnea, by supplying a continuous positive pressure to a patient's airway while the patient sleeps. A typical CPAP apparatus is programmed with a CPAP therapy pressure, and is able to maintain the set pressure (measured either at the mask or at a base unit) during the inhalation and exhalation phases of the breathing cycle. The pressure setting is typically programmed via a control on the unit. Bi-PAP machines will typically vary the positive pressure delivered to the user during the inhalation and exhalation phases of the breathing cycle. For purposes of this invention, it should be understood that the use of the term "CPAP" is meant to include both CPAP and Bi-PAP machines.

Referring now to FIG. 1, there is shown a typical prior art breathing gas delivery system 10. The breathing gas delivery system 10 comprises a control unit 12, a flexible tube 14, and a suitable device for directing air into the user's nasal passages, such as a patient interface 16. Patient interface 16, such as the mask-type shown in FIG. 1, is typically designed to cover the user's nose and/or mouth and forms an air-tight seal with the face of the user 18. The interface preferably includes adjustable straps 20 and 22 for adjusting the tightness of the interface on the face of the user 18. The control unit 12 includes a first switch 24 for turning on the breathing gas delivery system 10.

FIG. 2 shows a schematic view of a typical CPAP/Bi-PAP machine. Positive pressure is maintained by regulated blower 40 as shown in FIG. 2. Under control of motor control circuitry 38, blower 40 supplies a pressurized flow of air to the face mask 16 via the flexible tube 14. Regardless of whether the device is a CPAP machine or a Bi-PAP machine, microprocessor 34, in accordance with normal operating programming 50 produces motor control signal 37 which is interpreted by motor control circuitry 38. Motor control circuitry 38 translates motor control signal 37 into electrical impulses that control the speed of blower 40 to produce the desired pressure through flow element 42 and ultimately to the user of the device. The machine may be equipped with various sensors, such as pressure sensor 44, flow sensor 46 and/or motor current sensor 48.

The optimal pressure at which a CPAP machine is set often requires that a sleep study be performed on the patient. This approach utilizes a pressure titration in a sleep laboratory during an attended polysomnography, often requiring one or more overnight stays by the patient. The goal is to identify an effective pressure that will prevent apnea, hypopnia, snoring and respiratory effort-related arousals in all body positions and sleep stages, while still being tolerable by the patient. During the study, the technologist adjusts pressure to minimize events and to adjust for changes in body position and sleep stage.

As an alternative to a formal overnight sleep study with manual titration, auto-titrating devices have been developed. Such devices are designed to increase pressure as needed to maintain airway patency, and then to decrease pressure if no events are detected over a set period of time. Auto-adjusting CPAPs on the market today attempt to distinguish between obstructive sleep disordered breathing, which is treated with CPAP pressure, and central sleep disordered breathing, which is not treated well with CPAP pressure. The weakness of current CPAPs is that most sleep disordered breathing is treated with increasing pressure, even though increasing pressure may cause the patient to have an increase in central events. Reports from prior art CPAP devices may show, for example, event counts, but cannot evaluate when the delivery of CPAP pressure is not appropriate.

SUMMARY OF THE INVENTION

The present invention is a breathing therapy device having the ability to do patient phenotyping, also called titration phenotyping. This is the process of categorizing the patient's reaction to therapy while using an auto-titrating CPAP device. There are five categories that the machine of the present invention is capable of recognizing and reacting to. These are (1) linear obstructive; (2) non-responsive obstructive (non-linear); (3) central; (4) positional/REM; and (5) stable. The meaning of these categories and the machine's way the machine detects and reacts to them is discussed in more detail below.

This phenotyping of the patient's disorder is performed in real-time and may be reported to medical professionals in the form of a report. Analysis can also be performed off-line on recorded event, pressure and respiratory data. The patient phenotyping of the present invention accomplishes a novel report of how the patient's sleep disordered breathing responds to CPAP pressures, and can indicate if CPAP is the wrong therapy, for example, if the patient's condition does not improve with CPAP pressure. No current CPAP devices on the market categorize patients based on how the condition is treated with changing levels of CPAP pressure.

The device of the present invention creates a report of how the patient reacts in each of the five phenotype categories, indicating how well CPAP therapy is treating the patient. The report also generates a dynamic profile and a "respiratory phenotype map" of the patient across a single night or multiple nights, providing a confidence level of the patient's dominant phenotype as exhibited during the positive pressure therapy. The analysis may show variations in responses within a single night, and averaged over any desired duration from nights to years.

The device also has the ability to track disease evolution, body position effects, night-to-night variability, and treatment effects including non-pressure modalities such as medications. This approach can be utilized with other forms of positive pressure therapy, including adaptive and not adaptive bi-level ventilation.

The device of the present invention primarily utilizes a flow sensor to make a determination of the proper phenotype, but also may utilize external sensors for purposes of detecting central and/or obstructive type events.

BRIEF DESCRIPTION OF THE DRAWINGS

FIG. 4 as a chart representing one embodiment of an implementation of the logic in the phenotyping module which includes inputs, pressure change outputs and phenotype decision outputs.

DETAILED DESCRIPTION OF THE INVENTION

Figure 1:
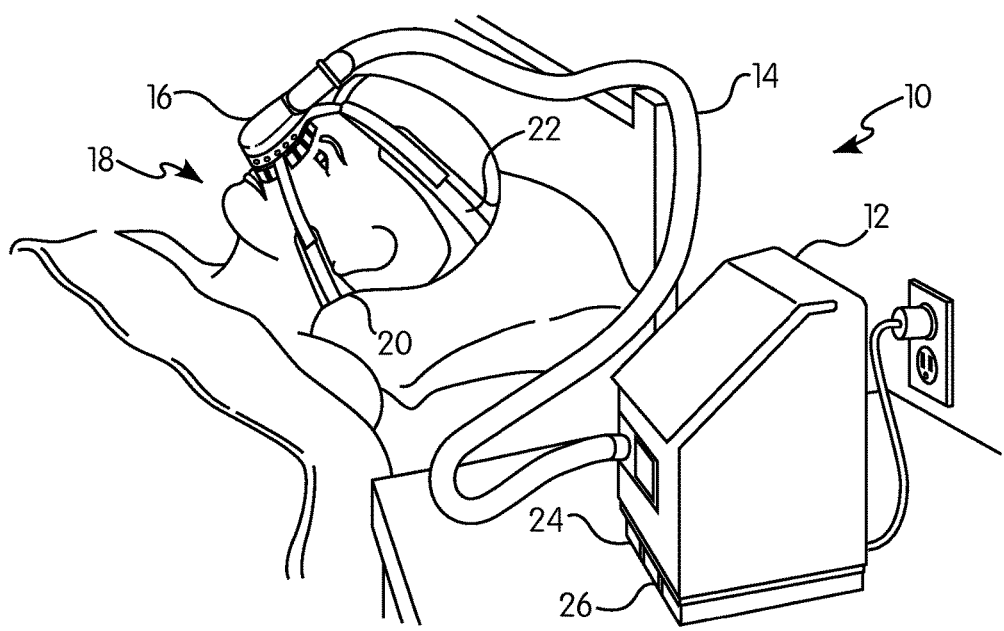
FIG. 1 is a schematic diagram of a prior art breathing therapy machine.
Figure 2:
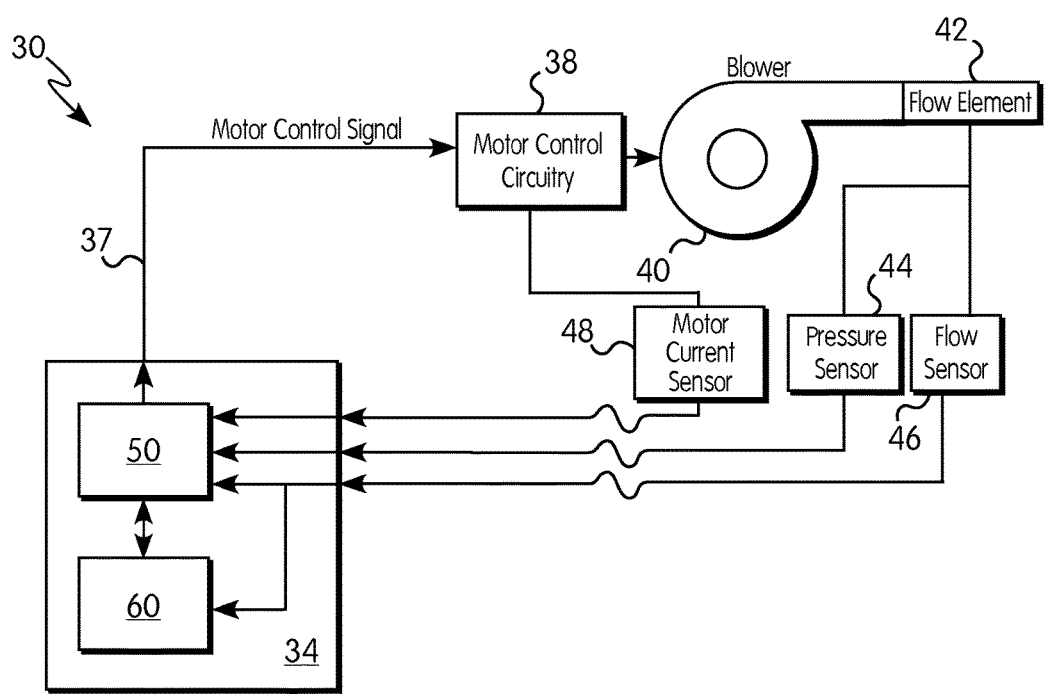
FIG. 2 is a block diagram is a typical breathing therapy machine having the components of the invention added therein.

FIG. 2 is a block diagram of a CPAP machine of the present invention. Normal operating module 50 include a data store which is capable of storing performance data of the machine for a period of operation. Such data may include, among other data, the number of hours the machine has been used, the number of obstructive and central events detected, the pressure settings of the machine and the average sensed pressure. The CPAP machine of the present invention has been modified from prior machines to include, in addition to normal operating module 50, a phenotyping module 60. Phenotyping module 60 preferably relies on flow sensor 46 to determine the patient's response to various CPAP pressures.

In one aspect of the invention, phenotyping module 60 works in conjunction with normal operating module 50 to provide an auto-titration mode that includes the ability to determine the therapeutic phenotype of the patient. The therapeutic phenotype is essentially an aggregate of the AHI (Apnea-Hypopnea Index) and pressure responses over time. Each therapeutic phenotype is accompanied by a corresponding confidence level determined by the amount of time or percent of time spent in each phenotype.

To determine the dominant phenotype, all of the phenotypes are scored with a probability level and the phenotype having the highest probability level will be determined as the dominant phenotype for the patient. The dominant phenotype is the one which best describes the pressure response of the patient's AHI profile. The various phenotypes are defined as follows:

Linear Obstructive Phenotype—Determined by a decrease in AHI and flow limitation of patient to increased pressure over time. This phenotype indicates that obstructions are being effectively treated with pressure increases in an essentially linear fashion.

Non-Responsive Obstructive Phenotype—Determined by a non-response in AHI and flow limitation of patient to increased pressure over time. This phenotype indicates that obstructions are not being effectively treated with pressure.

Positional or REM Obstructive Phenotype—Determined by occasional periods of high demand of increased pressure or decreased pressure due to positional changes (movements to or from supine) or rapid eye movement (REM) sleep stage transitions (transitions into or out of REM sleep). This phenotype indicates that obstructions are being effectively treated with periods of high increase or decrease of pressure.

Central (chemoreflex)—Determined by increase of AHI and flow limitation of patient to increased pressure over time. This phenotype indicates that the patient is not being effectively treated with pressure. There may or may not be simultaneous detection of central apneas and periodic breathing.

Stable Phenotype—Determined by stable breathing requiring little or no pressure adjustments. The stable phenotype is scored when none of the other four phenotype criteria are met.

In the preferred embodiment of the invention, the determination of the phenotype occurs in 3 minute intervals utilizing an analysis of data from the last rolling 9 minute period. That is, every 3 minutes a phenotype determination will be made and a tally added to the "score" of the determined phenotype. In addition, any pressure adjustments are also made on the same 3 minute cycle. As would be realized by one of skill in the art, other intervals utilizing data from different time periods may be utilized. In addition, the timing of the pressure adjustments may vary in alternate embodiments.

Figure 3:
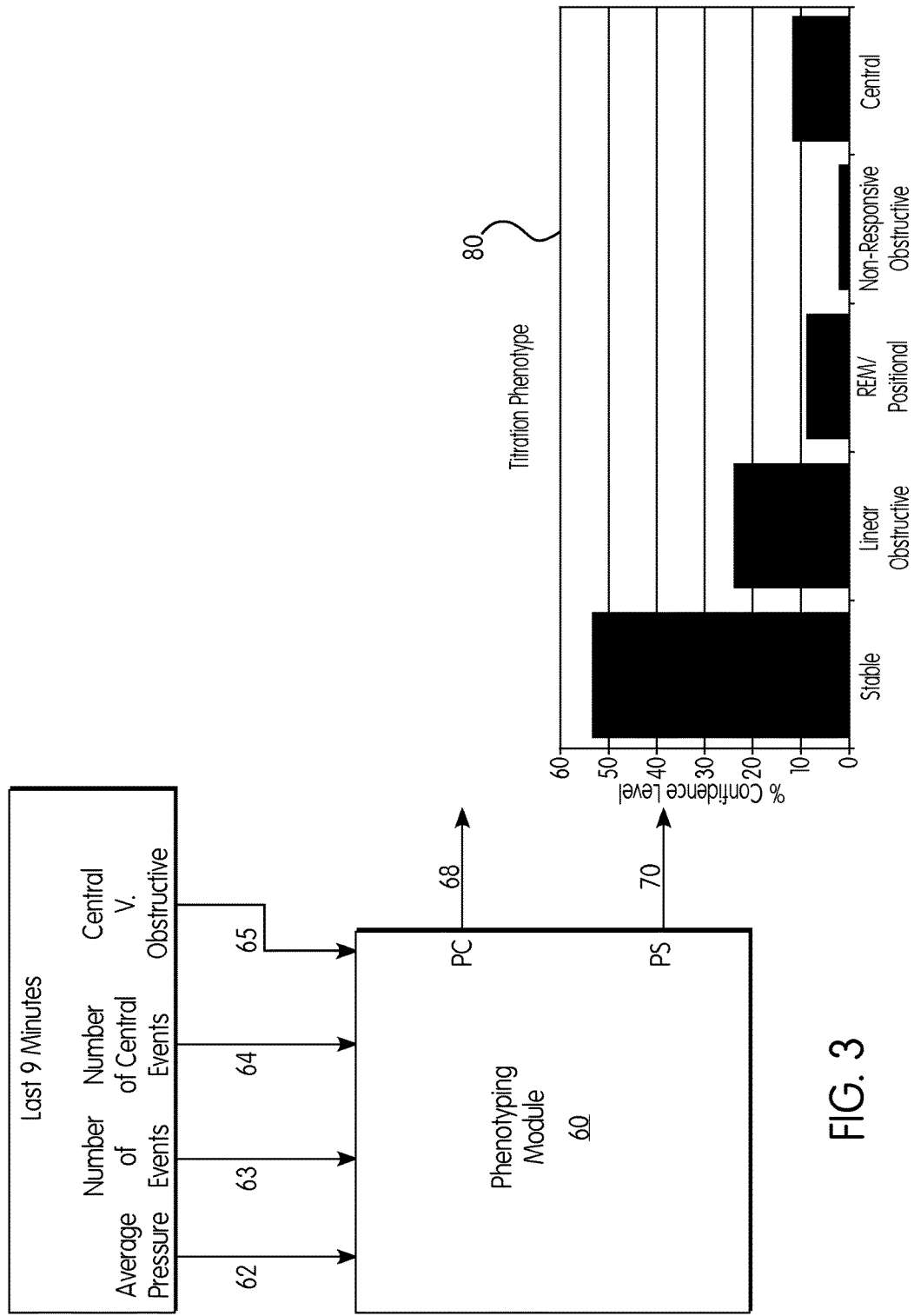
FIG. 3 is a block diagram of the phenotyping module showing the inputs and outputs.

FIG. 3 shows a block diagram of the phenotyping module, which utilizes data from the last rolling 9 minute period, including, in the preferred embodiment, the average pressure 62, the number of events 63, the number of central events 64 and a comparison to the number of central versus obstructive events 65. These inputs are analyzed by phenotyping module 60, and, in response, phenotyping module 60 produces a recommended pressure change 68, as well as a phenotype scoring decision 70. The logic used by preferred embodiment of phenotyping module 60 is captured in the table in FIG. 4. As would be realized by one of skill in the art, the logic involved in the analysis performed by phenotyping module 60, and the specific criteria used to score each phenotype, may vary from the preferred embodiment. The criteria shown in FIG. 4 and explained below for scoring phenotypes are only exemplary in nature. Different criteria for scoring each phenotype in various implementations of the invention could be used, and such implementations would still be within the scope of the invention.

Referring now to the table shown in FIG. 4, rows 1-3 and 6 show the conditions under which the stable phenotype is scored. If, during the last 9 minute time period, the average pressure and number of events is decreasing and the number of obstructive events is greater than the number of central events, then the stable phenotype will be scored. Additionally, the stable phenotype will be scored if the average pressure and the number of events is unchanged over the previous 9 minute time period. This phenotype indicates that the patient is being effectively treated by the therapy pressure and the pressure will be slightly reduced.

Rows 4 and 5 of the table of FIG. 4 show the conditions under which the linear obstructive phenotype is scored. Row 4 indicates that the average pressure over the last 9 minutes has increased, and a decrease in events has resulted. Row 5 indicates that the average pressure over the last 9 minutes has decreased, and the number of obstructive and central events has stayed the same. In general, the conditions in rows 4 and 5 are met if the patient is being effectively treated by the indicated pressure changes.

Row 7 of the table of FIG. 4 shows the conditions under which the non-responsive (non-linear) obstructive phenotype is scored. For this phenotype, the pressure is increasing, but the number of obstructive events is not decreasing. This indicates that the patient is not being effectively treated by the therapy pressure.

Rows 8-10 of the table of FIG. 4 shows the conditions under which the Positional/REM phenotype is scored. In general, this phenotype is characterized by an increase in obstructive events and is met by a larger increase in therapy pressure. In this phenotype, pressure is effectively treating the patient, with short period of high pressure required. It should also be noted that the Positional/REM phenotype is similar to the Linear Obstructive phenotype, but with a larger increase in pressure needed to counter the higher obstructive event density.

Finally, rows 11 and 12 of the table of FIG. 4 show the conditions under which the central phenotype is scored. In this phenotype, the number of central events is rising and/or has exceeded the number of obstructive events. This phenotype indicates that further increases in pressure are not effectively stopping the events, or are actually causing more central events.

It should be noted that the average pressure input to the phenotyping algorithm is the average pressure sensed by pressure sensor 44 and/or flow sensor 46 shown in FIG. 2.

It should be also noted that the phenotyping algorithm captured in FIG. 4 is only one example of a preferred embodiment of the invention and could be modified in other embodiments to include different inputs or different logic to determine the outputs.

Also in the preferred embodiment, the invention creates a report of how the patient reacted in each of the five phenotype categories. This indicates how well the CPAP therapy is treating the patient. In addition, in the preferred embodiment, a dynamic profile and respiratory phenotype map 80 of the patient across a single or multiple nights is generated. An example of this map is shown in FIG. 3 as reference number 80.

The respiratory phenotype map shows is essentially a bar chart showing the number of 3 minute intervals which were scored for each phenotype and would indicate the patient's dominant phenotype. The phenotype map 80 can easily show the dominant phenotype of the patient with a degree of confidence (depending on the size of the gap between the dominant phenotype and the next largest phenotype).

Also, in the preferred embodiment of the invention, the auto-adjusting therapy can be adjusted to respond more or less aggressively based upon the dominant phenotype which was detected.

In alternate embodiments of the invention, the stable phenotype may be omitted and the report would only include the other four phenotypes. In such a case, only four phenotypes are detected when determining the patient's dominant phenotype.

In yet another embodiment of the invention, other methods could be used to track and report the dominant phenotype. These include measuring the slopes of pressure changes versus AHI changes, wherein combinations of the pressure and AHI slopes can indicate a different pressure response and be classified as one of the phenotypes.

In other alternate embodiments, the CPAP machine may be equipped with a variety of external sensors, for example, EEG sensors which would aid in the detection of REM sleep phases, leg movement sensors, which would aid in the detection of the positional phenotype, chest effort sensors, which are useful in determining if central events are occurring, and many more. Such sensors could be connected to the CPAP machine via a wired or wireless interface.

It should also be noted that the invention, while described in the context of a CPAP machine, is also applicable to a Bi-PAP machine, having separate inhalation and exhalation pressure settings. In such a case, in one embodiment, the changes in exhalation pressure would track the changes in inhalation pressure. Additionally, the invention may be applicable to other type of breathing assist machines, such as respirators and ventilators.

We claim:

1. A breathing therapy machine having a phenotyping capability comprising:

a. a blower, for delivering pressurized air to a user of said device;
b. a processor, for controlling said blower;
c. non-volatile memory, accessible by said processor, said non-volatile memory containing an area for storage of performance data;
d. a phenotyping module, stored in said non-volatile memory, configured to perform the functions of:
periodically analyzing said performance data from a pre-determined period of operation of said machine;
determining a desired change in pressure based on said analysis of said performance data; and
adjusting said therapy pressure by said determined desired change, wherein the performance data includes:
an average pressure delivered to said user over said predetermined period of operation;
a change in a number of obstructive events in said pre-determined period of operation from a previous pre-determined period of operation;
a change in a number of central events in said pre-determined period of operation from a previous pre-determined period of operation; and
a comparison of the number of central events versus the number of obstructive events in said pre-determined period of operation, the phenotyping module configured to select a dominant phenotype of said user from a plurality of phenotypes for categorizing the user's reaction to pressure therapy, wherein the dominant phenotype is determined to be the phenotype that most accurately describes the user's response to therapy pressure and is selected by:
determining the phenotype of the plurality of phenotypes the user has during each of a plurality of analysis periods;
tallying the number of times each phenotype of the plurality of phenotypes is determined; and
selecting the phenotype having the highest tally to be the dominant phenotype of the user.

2. The breathing therapy machine of claim 1 wherein each of the plurality of analysis periods is 3 minutes.

3. The breathing therapy machine of claim 1 wherein said pre-determined period of operation is the last 9 minutes of operation.

4. The breathing therapy machine of claim 1 wherein said phenotyping module further performs the function of producing a respiratory phenotype map consisting of a chart showing the number of times each phenotype of the plurality of phenotypes was determined.

5. The breathing therapy machine of claim 1 wherein said phenotyping module further performs the function of producing a respiratory phenotype map consisting of a chart showing the percentage of time for which each phenotype was the determined phenotype.

6. The breathing therapy machine of claim 1 wherein the plurality of phenotypes includes at least one of stable, linear obstructive, positional/REM, non-responsive obstructive or central.

7. The breathing therapy machine of claim 1 wherein said determined phenotype is selected from a group consisting of linear obstructive, positional/REM, non-responsive obstructive and central.

8. The breathing therapy machine of claim 1 wherein said phenotype having been said determined phenotype for the most periods of analysis is the dominant phenotype and further wherein the normal operation of said breathing therapy machine is adjusted to respond based upon said dominant phenotype.

9. The breathing therapy machine of claim 1 wherein the phenotype is determined in each of the plurality of analysis periods based on the user's Apnea-Hypopnea Index and the user's response to a change in pressure of the pressurized air delivered to the user from the blower.

10. A method for determining a dominant phenotype of a user of a breathing therapy machine, the method comprising the steps of:
   a. collecting performance data for a rolling pre-determined period of operation of said machine;
   b. periodically analyzing said performance data from said pre-determined period of operation and determining a phenotype, of a plurality of phenotypes for categorizing the user's reaction to pressure therapy, the user has during each of a plurality of analysis periods;
   c. tallying the number of times each phenotype of the plurality of phenotypes is determined;
   d. selecting the phenotype having the largest tally to be the dominant phenotype of the user;
   e. determining a desired change in pressure based on said analysis of said performance data; and
   f. adjusting the pressure delivered by said breathing therapy machine based on said desired change in pressure;

wherein the dominant phenotype is determined to be the phenotype that most accurately describes the user's response to therapy pressure, wherein the performance data includes:
   an average pressure delivered to said user over said predetermined period of operation;
   a change in a number of obstructive events in said pre-determined period of operation from a previous pre-determined period of operation;
   a change in a number of central events in said pre-determined period of operation from a previous pre-determined period of operation; and
   a comparison of the number of central events versus the number of obstructive events in said pre-determined period of operation.

11. The method of claim 10 further comprising the step of producing a respiratory map consisting of a chart showing the number of times each phenotype of the plurality of phenotypes was determined or the percentage of time for which each phenotype was the determined phenotype.

12. The method of claim 10 further comprising the step of adjusting the normal operation of said breathing therapy machine to respond based upon said dominant phenotype.

\* \* \* \* \*